(12) United States Patent
Takemoto

(10) Patent No.: US 12,043,914 B2
(45) Date of Patent: Jul. 23, 2024

(54) METHOD FOR DISSOLVING TIN (II) OXIDE

(71) Applicant: JX Nippon Mining & Metals Corporation, Tokyo (JP)

(72) Inventor: Koichi Takemoto, Ibaraki (JP)

(73) Assignee: JX Metals Corporation, Tokyo (JP)

( * ) Notice: Subject to any disclaimer, the term of this patent is extended or adjusted under 35 U.S.C. 154(b) by 0 days.

(21) Appl. No.: 17/629,696

(22) PCT Filed: May 1, 2020

(86) PCT No.: PCT/JP2020/018453
§ 371 (c)(1),
(2) Date: Jan. 24, 2022

(87) PCT Pub. No.: WO2021/019862
PCT Pub. Date: Feb. 4, 2021

(65) Prior Publication Data
US 2022/0243349 A1 Aug. 4, 2022

(30) Foreign Application Priority Data

Aug. 1, 2019 (JP) .................................. 2019-142457
Oct. 11, 2019 (JP) .................................. 2019-188074

(51) Int. Cl.
*C25D 3/32* (2006.01)
*C07C 303/32* (2006.01)
(Continued)

(52) U.S. Cl.
CPC .............. *C25D 3/32* (2013.01); *C07C 303/32* (2013.01); *C07C 309/04* (2013.01); *C25D 3/30* (2013.01); *C25D 21/14* (2013.01)

(58) Field of Classification Search
None
See application file for complete search history.

(56) References Cited

U.S. PATENT DOCUMENTS

2003/0150743 A1  8/2003  Obata et al.
2010/0116674 A1  5/2010  Luo et al.
(Continued)

FOREIGN PATENT DOCUMENTS

EP  2578536 A2  4/2013
EP  3916132 A1  12/2021
(Continued)

OTHER PUBLICATIONS

International Search Report for PCT/JP2020/018453 dated Aug. 4, 2020, 5 pages.
(Continued)

*Primary Examiner* — Wojciech Haske
(74) *Attorney, Agent, or Firm* — Faegre Drinker Biddle & Reath LLP

(57) ABSTRACT

The present invention provides a method for producing an aqueous tin methanesulfonate solution by dissolving tin (II) oxide in an aqueous methanesulfonic acid solution, wherein if A is the number of moles of the tin (II) oxide and B is the number of moles of the methanesulfonic acid, the value of B/2A is within the range of from 1.0 to 1.4. This method for dissolving tin (II) oxide into an aqueous methanesulfonic acid solution is able to achieve a high tin ion concentration.

9 Claims, 7 Drawing Sheets

(51) Int. Cl.
*C07C 309/04* (2006.01)
*C25D 3/30* (2006.01)
*C25D 21/14* (2006.01)

(56) References Cited

U.S. PATENT DOCUMENTS

| | | |
|---|---|---|
| 2013/0084414 A1 | 4/2013 | Grandbois |
| 2013/0108512 A1 | 5/2013 | Grandbois |
| 2016/0348265 A1 | 12/2016 | Mayer et al. |
| 2017/0009632 A1 | 1/2017 | Seo |
| 2018/0274123 A1 | 9/2018 | Mayer et al. |
| 2022/0042196 A1* | 2/2022 | Tatsumi ................ C25D 21/12 |

FOREIGN PATENT DOCUMENTS

| | | | |
|---|---|---|---|
| JP | 200396590 A | 4/2003 | |
| JP | 2005314799 A | 11/2005 | |
| JP | 2009149979 A | 7/2009 | |
| JP | 2010133012 A | 1/2010 | |
| JP | 2010163667 A | 7/2010 | |
| JP | 5104253 B2 | 2/2013 | |
| JP | 201379186 A | 5/2013 | |
| JP | 5458555 B2 | 1/2014 | |
| JP | 20141410 A | 1/2014 | |
| JP | 201720102 A | 1/2017 | |
| JP | 2020143366 A | 9/2020 | |
| TW | 201323335 A1 | 6/2013 | |
| TW | 1464118 B | 12/2014 | |
| TW | 201710563 A | 3/2017 | |
| WO | WO-2020175352 A1 * | 9/2020 | ............... C25B 1/01 |

OTHER PUBLICATIONS

International Preliminary Examination Report for PCT/JP2020/018453 dated Aug. 1, 2019.
JP Office Action for corresponding JP Patent Application No. 2021-536616 dated Nov. 2, 2022 with Translation, 8 pages.
Extended European Search Report for the corresponding European Patent Application No. 20846082.4 dated Aug. 25, 2022, 8 pages.
Taiwan Office Action for corresponding Taiwan Patent Application No. 109117492 dated Aug. 4, 2021, 13 pages, with translation.
Korean Office Action for corresponding Korean Patent Application No. 10-2022-7006268, 10 pages, with translation, dated Mar. 18, 2024.

* cited by examiner

METHOD FOR DISSOLVING TIN (II) OXIDE

FIELD OF THE INVENTION

The present invention relates to a method for dissolving tin (II) oxide in an aqueous methanesulfonic acid solution to produce an aqueous tin methanesulfonate solution.

BACKGROUND OF THE INVENTION

When performing tin plating, an insoluble electrode (platinum, noble metal oxide, or the like) may be used in place of metallic tin as a positive electrode. In this case, a divalent tin ion solution is often added as a supplement with tin ions that are consumed from a plating solution. As the divalent tin ion solution, a tin methanesulfonate solution in which tin (II) oxide is dissolved in an aqueous methanesulfonic acid solution is used. It is preferable that the tin methanesulfonate solution has a higher tin ion concentration, because it is a solution for the supplement with tin ions.

Patent Literature 1 (Japanese Patent Application Publication No. 2003-96590 A) discloses a solution having a tin methanesulfonate concentration of 100 g/L as tin and a methanesulfonic acid concentration of 150 g/L in Examples.

Patent Literature 2 (Japanese Patent Application Publication No. 2005-314799 A) discloses a solution having a $Sn^{2+}$ ion concentration of 20 g/L and a methanesulfonic acid concentration of 30 mL/L in Examples.

Patent Literature 3 (Japanese Patent Application Publication No. 2010-163667 A) discloses a solution having a tin methanesulfonate concentration of 15 g/L as tin and a methanesulfonic acid concentration of 115 g/L as a free acid in Examples.

Patent Literature 4 (Japanese Patent No. 5104253 B) discloses that 20 g of SnO is dissolved in 300 mL of methanesulfonic acid at 25° C. in Comparison Test 1 in Examples.

Patent Literature 5 (Japanese Patent No. 5458555 B) discloses that 20 g of SnO is dissolved in 300 mL of methanesulfonic acid at 25° C. in Example 1.

CITATION LIST

Patent Literatures

[Patent Literature 1] Japanese Patent Application Publication No. 2003-96590 A
[Patent Literature 2] Japanese Patent Application Publication No. 2005-314799 A
[Patent Literature 3] Japanese Patent Application Publication No. 2010-163667 A
[Patent Literature 4] Japanese Patent No. 5104253 B
[Patent Literature 5] Japanese Patent No. 5458555 B

SUMMARY OF THE INVENTION

Technical Problem

As described above, it is preferable that the tin ion concentration is higher, because the tin methanesulfonate solution is a solution for supplementation with tin ions. However, all the tin ion concentrations in the tin methanesulfonate solutions disclosed in the prior arts are lower.

Therefore, an object of the present invention is to provide a method for dissolving tin (II) oxide in an aqueous methanesulfonic acid solution, which can achieve a higher tin ion concentration.

Solution to Problem

The present inventors have conducted intensive studies to solve the above problems. As a result, they have found that a higher tin ion concentration can be achieved by dissolving tin (II) oxide in an aqueous methanesulfonic acid solution by a method as described later, and have arrived at the present invention.

Therefore, the present invention includes the following aspect (1).

(1)
A method for dissolving tin (II) oxide in an aqueous methanesulfonic acid solution to produce an aqueous tin methanesulfonate solution,
wherein a value of B/2A is in a range of from 1.0 to 1.4, in which A is the number of moles of tin (II) oxide; and B is the number of moles of methanesulfonic acid.

Advantageous Effects of Invention

According to the present invention, it is possible to obtain a tin methanesulfonate solution which can be suitably used for supplementation with tin ions and has a higher tin ion concentration.

DETAILED DESCRIPTION OF THE INVENTION

Figure 1:
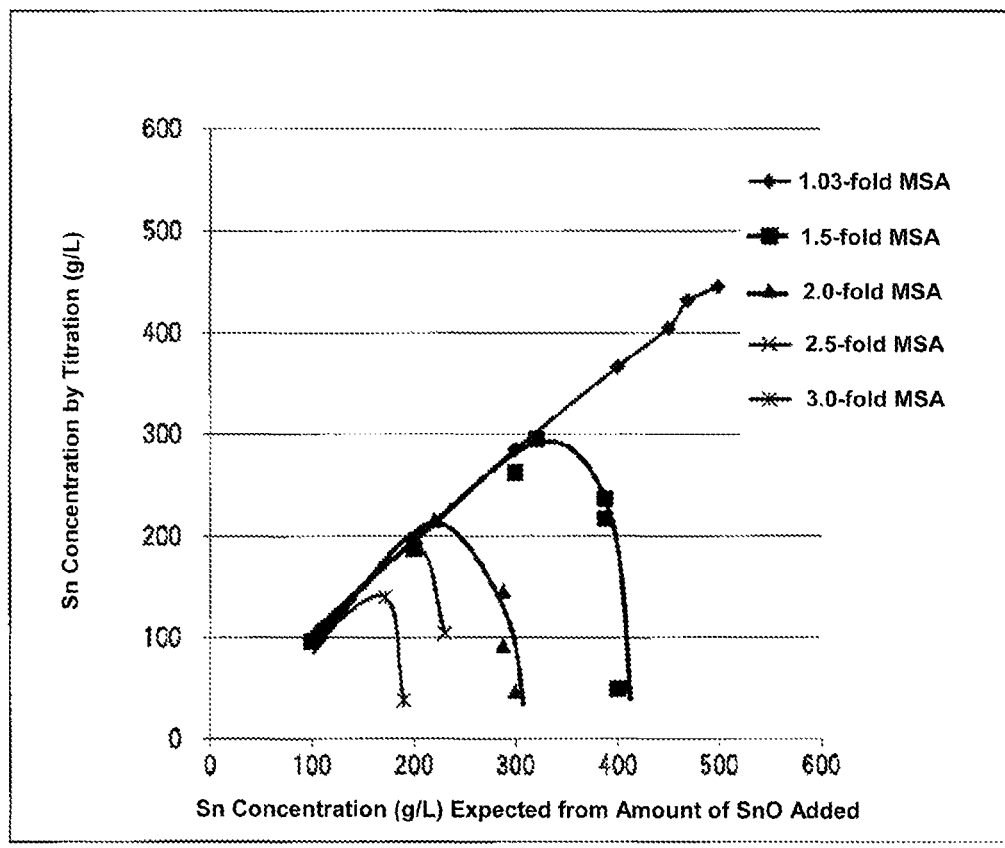
FIG. 1 shows a graph showing a relationship between a Sn concentration (g/L) expected from an amount of SnO added, and a Sn concentration (g/L) actually achieved, while comparing 1.03-fold MSA, 1.5-fold MSA, 2.0-fold MSA, 2.5-fold MSA, and 3.0-fold MSA in a dissolution experiment of tin (II) oxide in an aqueous methanesulfonic acid (MSA) solution.
Figure 2:
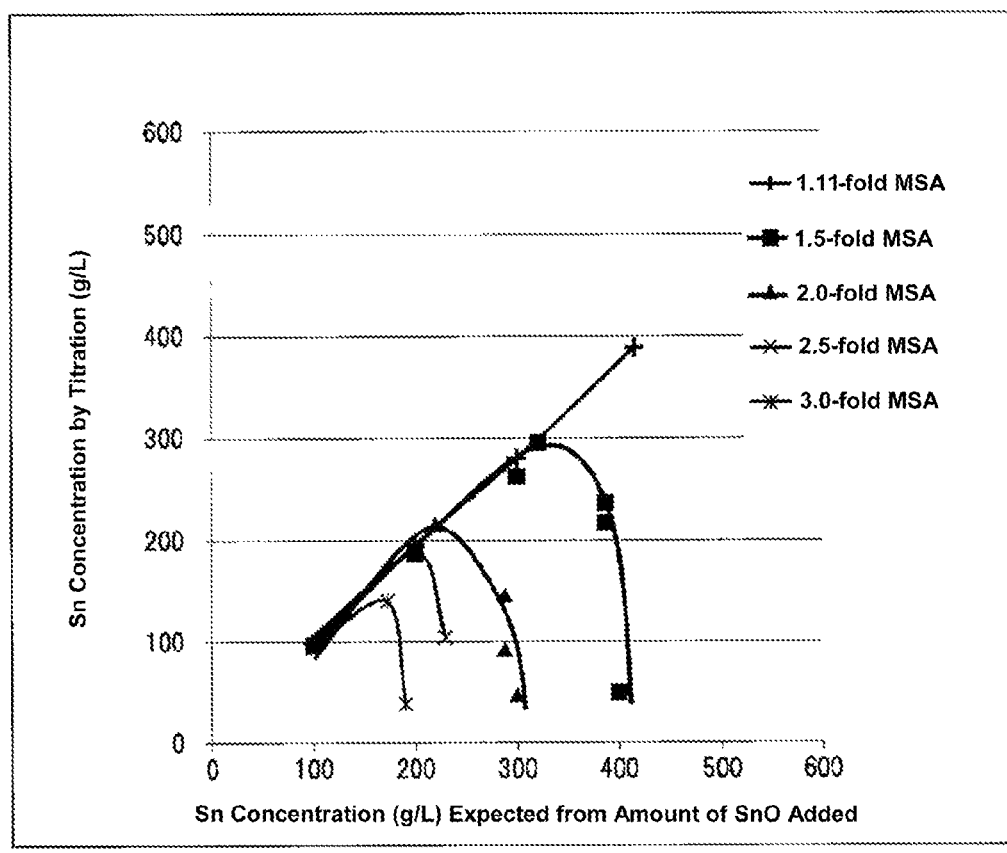
FIG. 2 shows a graph showing a relationship between a Sn concentration (g/L) expected from an amount of SnO added, and a Sn concentration (g/L) actually achieved, while comparing 1.11-fold MSA, 1.5-fold MSA, 2.0-fold MSA, 2.5-fold MSA, and 3.0-fold MSA in a dissolution experiment of tin (II) oxide in an aqueous methanesulfonic acid (MSA) solution.

Hereinafter, the present invention will be described in detail with reference to embodiments. The present invention is not limited to the specific embodiments listed below.

[Production of Aqueous Tin Methanesulfonate Solution]

According to the present invention, it is possible to produce an aqueous tin methanesulfonate solution having a higher tin ion concentration by a method for dissolving tin (II) oxide in an aqueous methanesulfonic acid solution to produce an aqueous tin methanesulfonate solution, wherein a value of B/2A is in a range of from 1.0 to 1.4, in which A is the number of moles of tin (II) oxide; and B is the number of moles of methanesulfonic acid.

[Value of B/2A]

The number of moles of tin (II) oxide used for dissolution is defined as A, and the number of moles of methanesulfonic acid used for dissolution is defined as B. In this case, by determining the number of moles of tin required to achieve the target tin concentration, the number of moles of methanesulfonic acid required for a dissolution reaction is determined according to a stoichiometric ratio in the dissolution reaction.

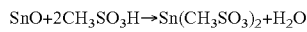

$$SnO+2CH_3SO_3H \rightarrow Sn(CH_3SO_3)_2+H_2O$$

Therefore, when using methanesulfonic acid in which the number of moles is 1.0 times the number of moles of methane sulfonic acid required for the reaction, which is determined according to the stoichiometric ratio from the number of moles of tin required, the value of B/2A will be 1.0. Similarly, when using methanesulfonic acid in which the number of moles is 1.1 times the number of moles of methanesulfonic acid required for the reaction, which is determined according to the stoichiometric ratio from the number of moles of tin required, the value of B/2A will be 1.1. Thus, the value of B/2A is an indicator of how many times the number of moles of methanesulfonic acid was used relative to the number of moles of methanesulfonic acid required according to the stoichiometric ratio of the reaction. As used herein, when the value of B/2A is n, it may be denoted as n-fold MSA.

In a suitable embodiment, the number of moles A of tin (II) oxide used for dissolution refers to the number of moles of the total amount of tin (II) oxide used for dissolution, and the number of moles B of methanesulfonic acid used for dissolution refers to the number of moles of the total amount of methanesulfonic acid used for dissolution.

As is well known, when a substance is to be dissolved by a chemical reaction in a solution, it is expected that a target substance will also be dissolved at a higher concentration by increasing a concentration of a solute in the solution, which is the counterpart of the chemical reaction. In a case of dissolving tin (II) oxide in an aqueous methanesulfonic acid solution, it has been generally believed that a higher concentration of methanesulfonic acid could achieve a higher tin ion concentration.

However, as indicated by results of experiments in Examples as described below, the present inventors have found that there is a concentration condition where the higher tin ion concentration can be achieved in a range where a concentration of methanesulfonic acid, which is in excess of the theoretical reaction amount stoichiometrically required, is rather lower. According to this finding, when the value of B/2A in which A is the number of moles of tin (II) oxide and B is the number of moles of methanesulfonic acid is in the above range, the higher tin ion concentration can be achieved by approaching a stoichiometric theoretical reaction amount rather than by further increasing the concentration of methanesulfonic acid.

In a preferred embodiment, the value of B/2A may be, for example, in a range of from 1.00 to 1.40, preferably in a range of from 1.01 to 1.40, or in a range of from 1.02 to 1.40, or in a range of from 1.03 to 1.40.

In a preferred embodiment, the value of B/2A may be, for example, in a range of from 1.00 to 1.30, preferably in a range of from 1.01 to 1.30, or in a range of from 1.02 to 1.30, or in a range of from 1.03 to 1.30.

In a preferred embodiment, the value of B/2A may be, for example, in a range of from 1.00 to 1.20, preferably in a range of from 1.01 to 1.20, or in a range of from 1.02 to 1.20, or in a range of from 1.03 to 1.20.

In a preferred embodiment, the value of B/2A may be, for example, in a range of from 1.00 to 1.15, preferably in a range of from 1.01 to 1.15, or in a range of from 1.02 to 1.15, or in a range of from 1.03 to 1.15.

In a preferred embodiment, the value of B/2A may be, for example, in a range of from 1.00 to 1.12, preferably in a range of from 1.01 to 1.12, or in a range of from 1.02 to 1.12, or in a range of from 1.03 to 1.12.

In a preferred embodiment, the value of B/2A may be, for example, in a range of from 1.00 to 1.11, preferably in a range of from 1.01 to 1.11, or in a range of from 1.02 to 1.11, or in a range of from 1.03 to 1.11.

In a preferred embodiment, the value of B/2A may be, for example, in a range of from 1.00 to 1.10, preferably in a range of from 1.01 to 1.10, or in a range of from 1.02 to 1.10, or in a range of from 1.03 to 1.10.

In a preferred embodiment, the value of B/2A may be, for example, in a range of from 1.00 to 1.09, preferably in a range of from 1.01 to 1.09, or in a range of from 1.02 to 1.09, or in a range of from 1.03 to 1.09.

In a preferred embodiment, the value of B/2A may be, for example, in a range of from 1.00 to 1.08, preferably in a range of from 1.01 to 1.08, or in a range of from 1.02 to 1.08, or in a range of from 1.03 to 1.08.

In a preferred embodiment, the value of B/2A may be, for example, in a range of from 1.00 to 1.07, preferably in a range of from 1.01 to 1.07, or in a range of from 1.02 to 1.07, or in a range of from 1.03 to 1.07.

In a preferred embodiment, the value of B/2A may be, for example, in a range of from 1.00 to 1.06, preferably in a range of from 1.01 to 1.06, or in a range of from 1.02 to 1.06, or in a range of from 1.03 to 1.06.

In a preferred embodiment, the value of B/2A may be, for example, in a range of from 1.00 to 1.05, preferably in a range of from 1.01 to 1.05, or in a range of from 1.02 to 1.05, or in a range of from 1.03 to 1.05.

In a preferred embodiment, the value of B/2A may be, for example, in a range of from 1.00 to 1.04, preferably in a range of from 1.01 to 1.04, or in a range of from 1.02 to 1.04, or in a range of from 1.03 to 1.04.

In a preferred embodiment, the value of B/2A may be, for example, in a range of from 1.00 to 1.03, preferably in a range of from 1.01 to 1.03, or in a range of from 1.02 to 1.03.

[Tin (II) Oxide]

Tin (II) oxide used is not particularly limited, and commercially available tin (II) oxide can be used. In a preferred embodiment, tin (II) oxide can be in the form of powder. Any powder form can be used without particular limitation as long as it is suitable for the dissolution operation. For example, powder having an average particle diameter in a range of from 1 μm to 100 μm can be used.

[Methanesulfonic Acid]

Methanesulfonic acid used is not particularly limited, and commercially available methanesulfonic acid can be used. In a preferred embodiment, the methanesulfonic acid can be used in the form of an aqueous methanesulfonic acid solution. In a preferred embodiment, the concentration of methanesulfonic acid in the aqueous methanesulfonic acid solution is determined depending on the target dissolved tin ion concentration and the value of B/2A, as described above.

[Addition and Stirring of Tin (II) Oxide Powder]

In a preferred embodiment, the tin (II) oxide powder can be added to an aqueous methanesulfonic acid solution, stirred and dissolved to produce an aqueous tin methanesulfonate solution. The addition and stirring can be carried out using known means. The adding and stirring operations are carried out until the tin (II) oxide powder is dissolved. The dissolution can be visually detected, because the black stannous oxide powder becomes colorless and transparent upon dissolution. In a preferred embodiment, the adding and stirring operations can be carried out over, for example, 0.1 to 60 minutes, 1 to 30 minutes, or 1 to 10 minutes, although it depends on the total amount. In a preferred embodiment, a temperature of the solution during dissolution may be, for example, in a range of from 10 to 80° C., or for example, in a range of from 20 to 60° C., although not particularly limited thereto.

[Aqueous Tin Methanesulfonate Solution]

According to the present invention, tin (II) oxide can be dissolved in an aqueous methanesulfonic acid solution to produce an aqueous tin methanesulfonate solution. The resulting aqueous tin methanesulfonate solution contains a higher concentration of tin in the form of $Sn^{2+}$ ions.

In a preferred embodiment, the content of tin present as $Sn^{2+}$ ions in the aqueous tin methanesulfonate solution may be, for example, in a range of from 200 to 450 g/L, preferably in a range of from 250 to 450 g/L, preferably in a range of from 300 to 450 g/L, preferably in a range of from 350 to 450 g/L, or in a range of from 200 to 430 g/L, preferably in a range of from 250 to 430 g/L, preferably in a range of from 300 to 430 g/L, preferably in a range of from 350 to 430 g/L.

In a preferred embodiment, the content of methanesulfonic acid in the aqueous tin methanesulfonic acid solution is determined from the value of B/2A as described above and the tin content. In a preferred embodiment, the content of methanesulfonic acid present as methanesulfonic acid ions in the aqueous tin methanesulfonate solution may be, for example, in a range of from 0.1 to 100 g/L, or in a range of from 0.1 to 70 g/L, or in a range of from 0.1 to 50 g/L, or in a range of from 0.1 to 40 g/L, or in a range of from 0.1 to 30 g/L, or in a range of from 0.1 to 25 g/L, or in a range of from 0.1 to 20 g/L.

[Supplement of Tin Plating Solution with Tin Ions]

In a preferred embodiment, the aqueous tin methanesulfonate solution produced by the present invention has a higher content of tin present as $Sn^{2+}$ ions. When tin plating is performed using an insoluble electrode (platinum, noble metal oxide, or the like) in place of metallic tin as a positive electrode, the tin ions are consumed from a plating solution. Therefore, the aqueous tin methanesulfonate solution can be suitably used for supplementing such a tin plating solution with the tin ions by utilizing the characteristic of higher concentration of $Sn^{2+}$ ions. Therefore, the present invention includes a method for adding an aqueous tin methanesulfonate solution produced by the present invention to a tin plating solution to supplement the tin plating solution with the tin ions. Furthermore, the present invention includes a method for producing a tin plating solution thus supplemented with the tin ions.

Preferred Embodiment

In a preferred embodiment, the present invention may include the following aspects (1) to (10):

(1)

A method for dissolving tin (II) oxide in an aqueous methanesulfonic acid solution to produce an aqueous tin methanesulfonate solution, wherein a value of B/2A is in a range of from 1.0 to 1.4, in which A is the number of moles of tin (II) oxide; and B is the number of moles of methanesulfonic acid.

(2)

The method according to (1), wherein the tin (II) oxide is tin (II) oxide powder.

(3)

The method according to (1) or (2), wherein the value of B/2A is in a range of from 1.01 to 1.4.

(4)

The method according to any one of (1) to (3), wherein the tin (II) oxide powder is added to the aqueous methanesulfonic acid solution, stirred and dissolved to produce an aqueous tin methanesulfonate solution.

(5)

The method according to any one of (1) to (4), wherein when tin (II) oxide is completely dissolved in the aqueous methanesulfonic acid solution, a content of tin present as $Sn^{2+}$ ions is in a range of from 300 to 450 g/L.

(6)

The method according to any one of (1) to (5), wherein the number of moles of tin (II) oxide A is the number of moles of the total amount of tin (II) oxide used for dissolution, and wherein the number of moles of methanesulfonic acid B is the number of moles of the total amount of methanesulfonic acid used for dissolution.

(7)

A method for supplementing a tin plating solution with tin ions, the method comprising a step of adding the aqueous tin methanesulfonate solution produced by the method according to any one of (1) to (6) to the tin plating solution.

(8)

A method for producing a tin plating solution supplemented with tin ions by the method according to (7).

(9)

An aqueous tin methanesulfonate solution, wherein a content of tin present as $Sn^{2+}$ ions is in a range of from 300 to 450 g/L.

(10)

The aqueous tin methanesulfonate solution according to (9), wherein the aqueous tin methanesulfonate solution is an aqueous tin methanesulfonate solution for supplementing a tin plating solution with tin ions.

EXAMPLES

Hereinafter, the present invention will be described in more detail with reference to Examples. The present invention is not limited to the following Examples.

Example 1: Preparation of Tin Methanesulfonate Solution Having Higher Concentration by Dissolution of Tin (II) Oxide In order to prepare a tin methanesulfonate solution having a higher concentration, an operation of adding tin (II) oxide powder to an aqueous methanesulfonic acid solution to dissolve it was carried out by setting the conditions as follows:

As the tin (II) oxide powder, a commercially available tin (II) oxide powder (HK 0040 active tin (II) oxide from JX Metals Trading Co., Ltd.) was prepared.

As the aqueous methanesulfonic acid solution, a commercially available aqueous methanesulfonic acid solution (from JX Metals Trading Co., Ltd., trade name: NSP-A700M, a methanesulfonic acid concentration of 68% by mass) was prepared.

[Determination of Target Tin Concentration and Amount of Tin (II) Oxide Used]

An amount of the tin methanesulfonate solution having a higher concentration to be prepared was 100 mL.

A plurality of concentrations (for example, 300 g/L) were set as the target higher tin concentrations ($Sn^2$ ion concentrations).

An amount of Sn required to achieve each of the above target tin concentrations was calculated.

For example, the amount of Sn required to bring the tin concentration to 300 g/L in 100 mL is 30 g.

A mass of tin (II) oxide powder required to achieve each of the above tin concentrations was calculated.

For example, when the tin (II) oxide powder is a wet product and a Sn quality of 86%, the mass of tin (II) oxide powder required to bring the tin concentration to 300 g/L in 100 mL will be as follows: 30.0 g/0.86=34.88→about 34.9 g.

[Determination of Amount of MSA Used]

Tin (II) oxide (which may, hereinafter, be referred to as SnO) reacts with methanesulfonic acid ($CH_3SO_3H$) as follows to dissolve it.

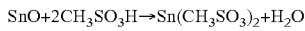

Thus, SnO is dissolved in MSA at a molar ratio of SnO:MSA=1:2.

Therefore, if the number of moles of tin is determined from the value of the amount of tin required to achieve each target tin concentration, the number of moles of methanesulfonic acid required for the reaction can also be determined according to the stoichiometric ratio as described above. When using methanesulfonic acid in which the number of moles is 1.0 times the required number of moles of methanesulfonic acid thus determined, an amount of methanesulfonic acid used may be expressed as 1.0-fold MSA in the present application. Similarly, when using methanesulfonic acid in which the number of moles is 1.1 times the number of moles of methanesulfonic acid required according to the stoichiometric ratio in the above dissolution reaction, an amount of methanesulfonic acid used may be expressed as 1.1-fold MSA in the present application. These 1.0-fold MSA, 1.1-fold MSA, and the like may be collectively referred to as n-fold MSA in the present application.

For the above MSA amount set corresponding to the amount of tin required to achieve each target tin concentration, a plurality of MSA amounts were set for each of the required tin amounts to examine how the tin (II) oxide was dissolved when a value of each MSA amount was used. The MSA amount corresponding to each set MSA amount (e.g., 1.0-fold MSA, 1.1-fold MSA, and the like) was calculated.

For example, in a case of 1.0-fold MSA for a tin amount of 30 g, the specific gravity will be 1.38 when the concentration of the MSA solution is 68%. The atomic weight of tin is 118.7 and the molecular weight of MSA is 96.1. Therefore, an amount of the MSA solution added is calculated as follows: 30.0 g/118.7×192.2/1.38/0.98×1.0=51.76 mL→about 51.8 mL.

[Determination of Amount of Pure Water Added]

In addition to each mass of the tin (II) oxide powder to be added and each volume of the MSA solution to be used, which were calculated by the above procedure, the addition of pure water was required to achieve the above target tin concentrations. For the addition of pure water, a rough estimate of the maximum amount of pure water to be added was previously calculated by subtracting each volume of the MSA solution from 100 mL, and prior to the addition of the tin (II) oxide, the majority of the pure water to be used was mixed with the MSA solution in advance, and after the addition of the tin (II) oxide, the solution was further adjusted by scale-up to a final volume of 100 mL so that the solution after the reaction was a predetermined volume (100 mL).

[Operation of Dissolution]

Pure water was added to a predetermined volume of the MSA solution as needed, and the temperature was then brought to about 30° C. by natural cooling.

To the aqueous MSA solution was sequentially added a predetermined mass of tin (II) oxide powder with stirring to dissolve it over a total period time of 3 minutes. The temperature in this case was maintained in the range of from about 30 to 50° C. As the whole amount of the black tin (II) oxide powder was dissolved, the dissolution was considered to be completed at that time. Also, if it was not dissolved even after 3 minutes, the dissolution operation was further continued, and the dissolution operation was terminated at the time when 5 minutes was elapsed.

At the end of the dissolution operation, the tin methanesulfonate solution (MSA-Sn solution) was collected and adjusted to the defined volume (100 mL) by adding pure water to scale-up. The tin concentration ($Sn^2$ ion concentration) was measured by redox titration using iodine-starch reaction for the resulting tin methanesulfonate solution having the defined volume.

Example 2: Preparation of Tin Methanesulfonate Solution Having Higher Concentration by Dissolving Tin (II) Oxide in Aqueous Methanesulfonic Acid Having Higher Concentration Using an aqueous methanesulfonic acid solution having a higher concentration (from Fujifilm Wako Chemicals Corporation, Wako special grade, a methanesulfonic acid concentration of 98% by mass) in place of the aqueous methanesulfonic acid solution used in Example 1, the same experiment was conducted under a condition of 1.03-fold MSA.

Results of Example 1 and Example 2

Figure 3:
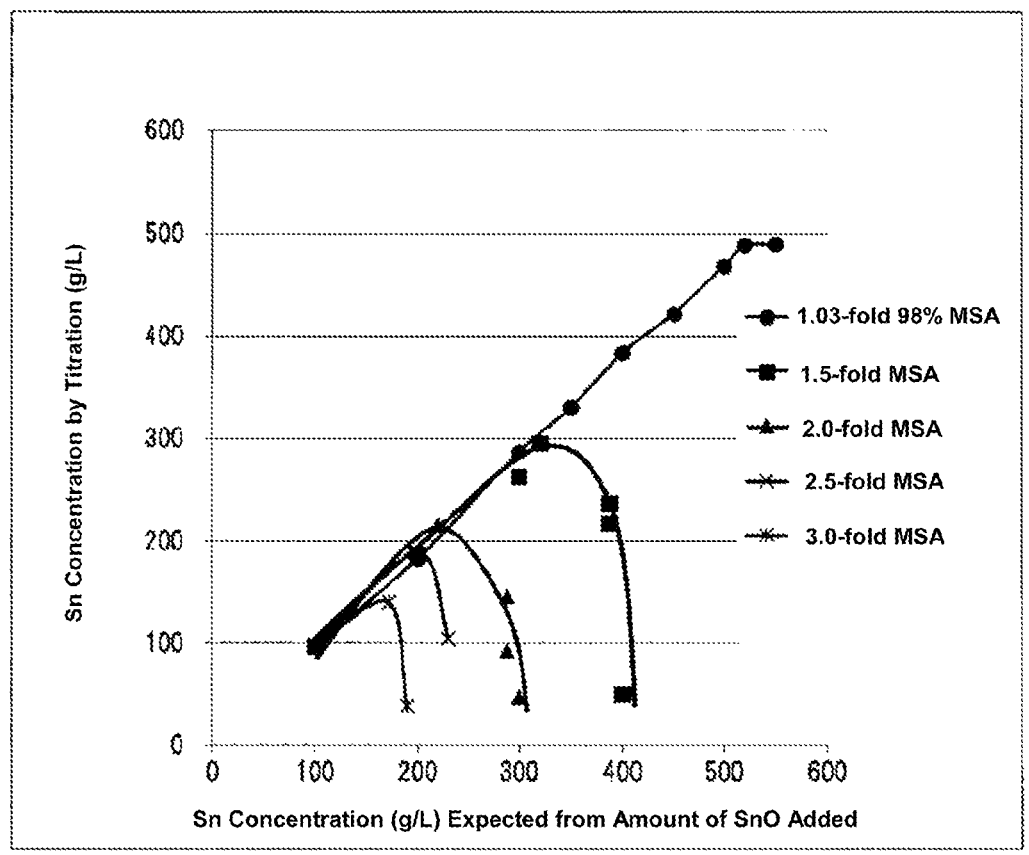
FIG. 3 shows a graph showing a relationship between a Sn concentration (g/L) expected from an amount of SnO added, and a Sn concentration (g/L) actually achieved, while comparing 1.03-fold 98% MSA, 1.5-fold MSA, 2.0-fold MSA, 2.5-fold MSA and 3.0-fold MSA in a dissolution experiment of tin (II) oxide in an aqueous methanesulfonic acid (MSA) solution.
Figure 4:
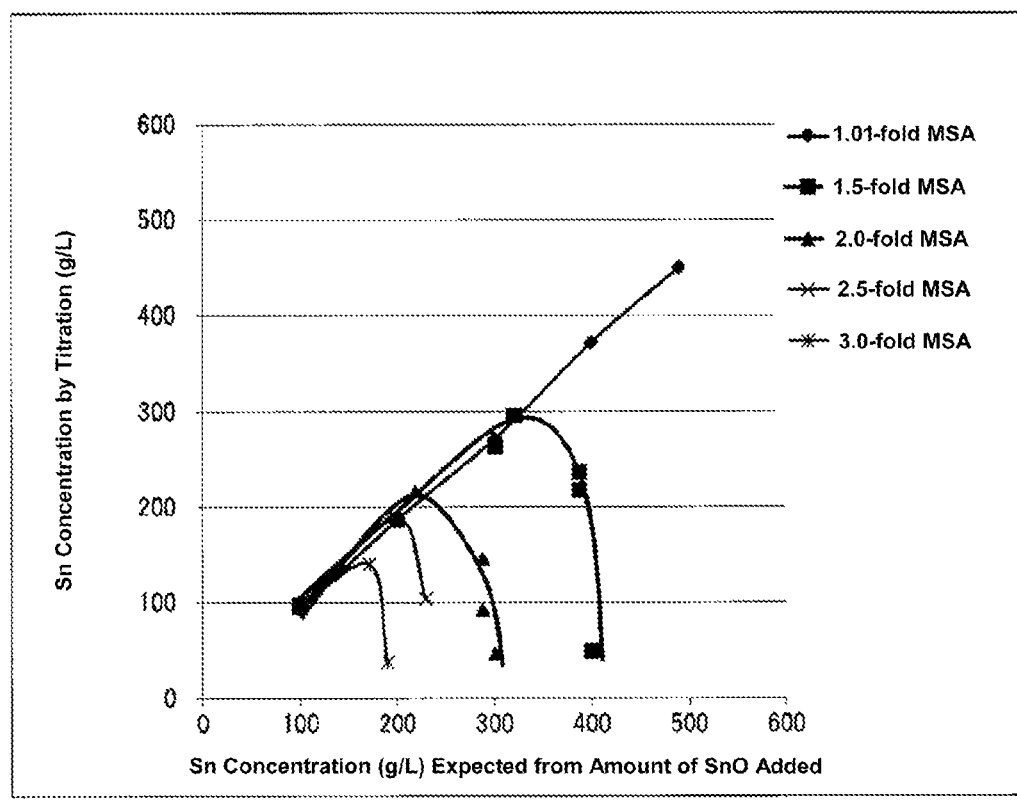
FIG. 4 shows a graph showing a relationship between a Sn concentration (g/L) expected from an amount of SnO added, and a Sn concentration (g/L) actually achieved, while comparing 1.01-fold MSA, 1.5-fold MSA, 2.0-fold MSA, 2.5-fold MSA, and 3.0-fold MSA in a dissolution experiment of tin (II) oxide in an aqueous methanesulfonic acid (MSA) solution.
Figure 5:
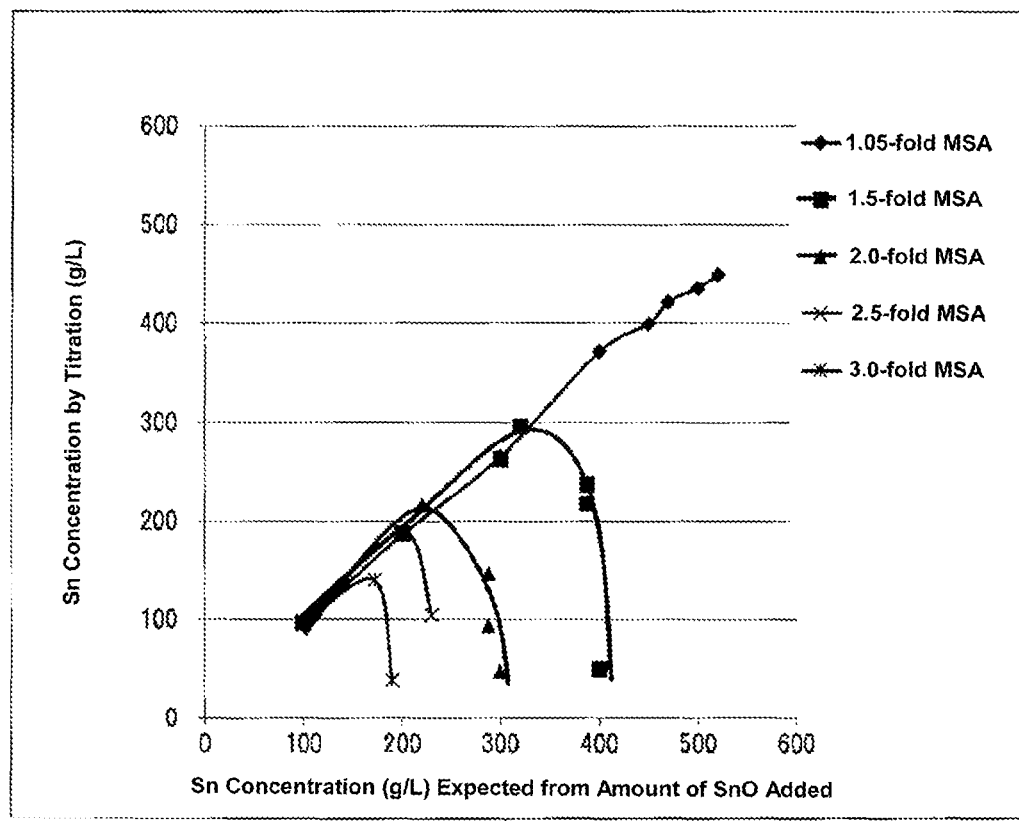
FIG. 5 shows a graph showing a relationship between a Sn concentration (g/L) expected from an amount of SnO added, and a Sn concentration (g/L) actually achieved, while comparing 1.05-fold MSA, 1.5-fold MSA, 2.0-fold MSA, 2.5-fold MSA, and 3.0-fold MSA in a dissolution experiment of tin (II) oxide in an aqueous methanesulfonic acid (MSA) solution.
Figure 6:
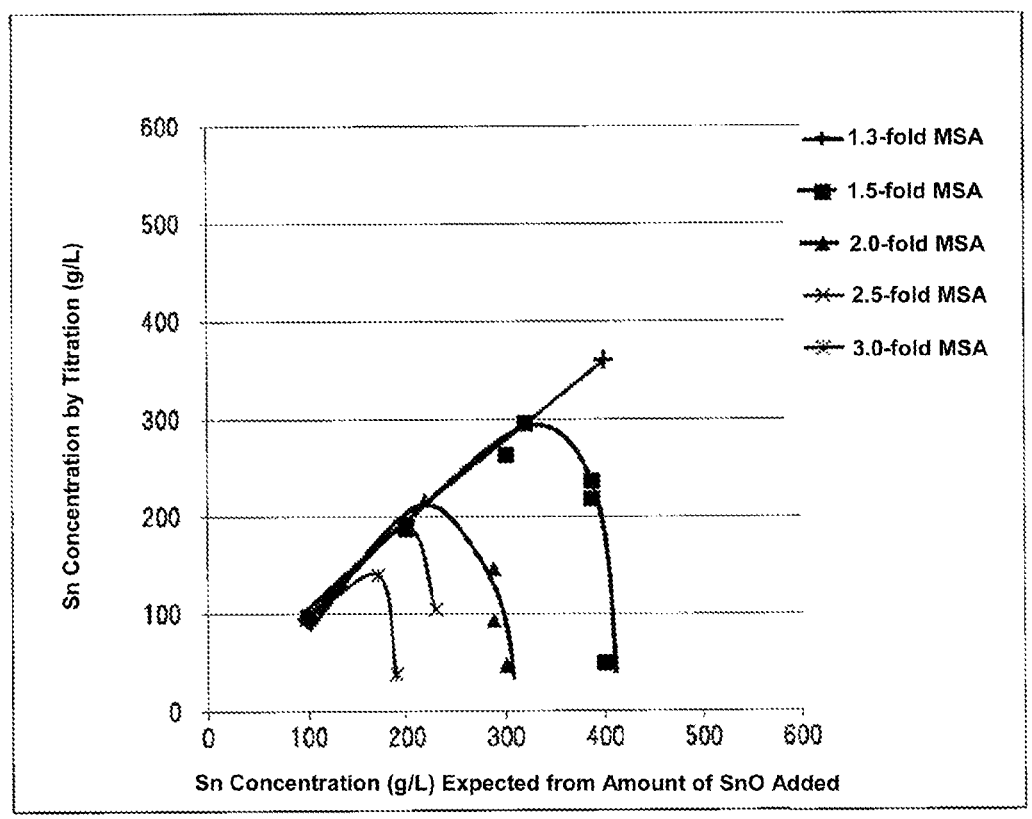
FIG. 6 shows a graph showing a relationship between a Sn concentration (g/L) expected from an amount of SnO added, and a Sn concentration (g/L) actually achieved, while comparing 1.3-fold MSA, 1.5-fold MSA, 2.0-fold MSA, 2.5-fold MSA, and 3.0-fold MSA in a dissolution experiment of tin (II) oxide in an aqueous methanesulfonic acid (MSA) solution.
Figure 7:
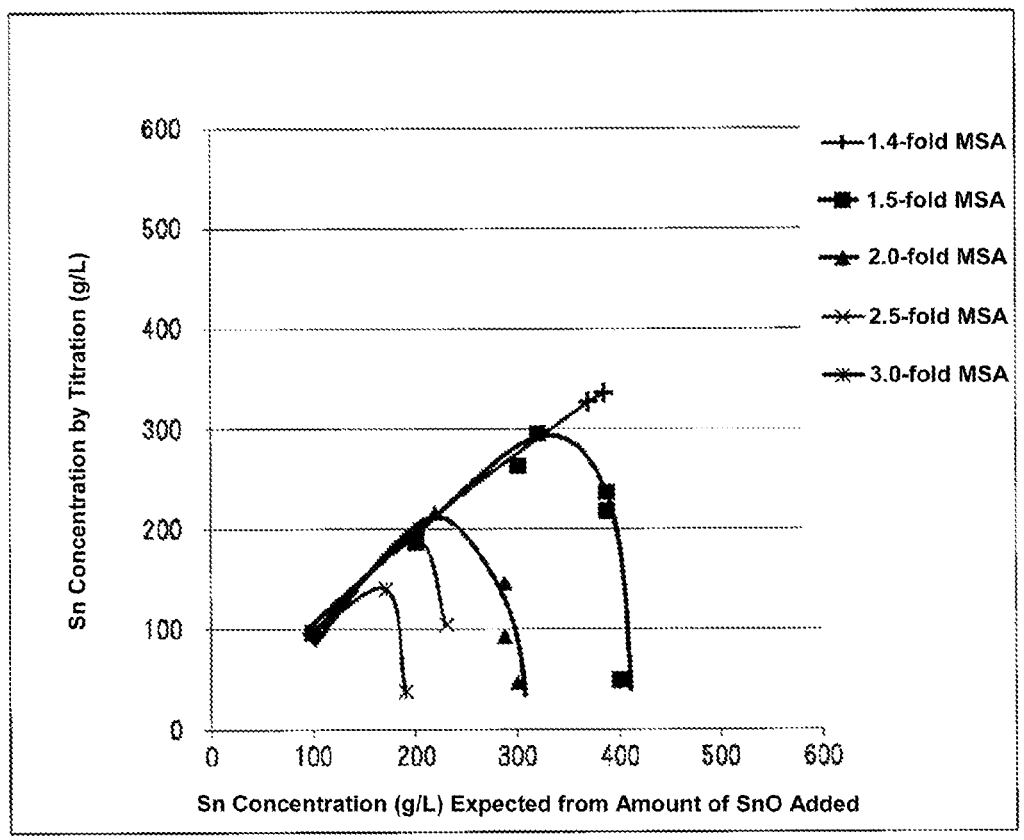
FIG. 7 shows a graph showing a relationship between a Sn concentration (g/L) expected from an amount of SnO added, and a Sn concentration (g/L) actually achieved, while comparing 1.4-fold MSA, 1.5-fold MSA, 2.0-fold MSA, 2.5-fold MSA, and 3.0-fold MSA in a dissolution experiment of tin (II) oxide in an aqueous methanesulfonic acid (MSA) solution.

The results obtained by the experiments of Examples 1 and 2 are shown in FIGS. 1 to 7. Each point in each graph shows a measured value obtained by the dissolution experiment by the combination of the amount of the oxide (II) powder used and the amount of methanesulfonic acid used set by the above procedure. The horizontal axis of the graph in each of FIGS. 1 to 7 is a $Sn^{2+}$ ion concentration [g/L] in the solution calculated assuming that the whole amount of the added tin (II) oxide powder was dissolved. The vertical axis of the graph in each of FIGS. 1 to 7 is a $Sn^{2+}$ ion concentration [g/L] measured by titrating the actually obtained solution. For example, the 1.03-fold MSA shown in FIG. 1 refers to a case where the amount of methanesulfonic acid as described above was 1.03-fold MSA amount, which means that methanesulfonic acid in which the number of moles was 1.03 times the number of moles of methanesulfonic acid required from the stoichiometric ratio where the added tin (II) oxide reacted with methanesulfonic acid to produce tin methanesulfonate. The same is true for 1.5-fold MSA, 2.0-fold MSA, 2.5-fold MSA, and 3.0-fold MSA. The data of 1.03-fold 98% MSA shown in FIG. 3 is the result of conducting an experiment at a higher concentration (98% by mass) of methanesulfonic acid according to Example 2. All date having no particular mention are results when the experiment was carried out according to Example 1. In FIGS. 1 to 7, for comparison, the same contents are shown for the data of Comparative Examples.

As can be seen from the graph in FIG. 1, in the case of 1.03-fold MSA, the whole amount of tin (II) oxide added to the aqueous methanesulfonic acid solution was dissolved as it was, and an aqueous tin methanesulfonate solution with a higher concentration of $Sn^{2+}$ ions up to 450 [g/L] was obtained. As can be seen from the graph in FIG. 3, this result was also the same in the case where the higher concentration MSA of 98% by mass was used in Example 2 (1.03-fold 98% MSA). Also, as can be seen from the graphs in FIG. 2, FIG. 6, and FIG. 7, the same was true for the cases of 1.11-fold MSA, 1.3-fold MSA, and 1.4-fold MSA in Example 1. Furthermore, as can be seen from the graph in FIG. 4, in the case of 1.01-fold MSA in Example 1, the solubility was particularly improved. As can be seen from the graph in FIG. 5, the same was true for 1.05-fold MSA in Example 1.

On the other hand, as can be seen from the graphs in FIGS. 1 to 7, for the use of 1.5-fold MSA, the whole amount of tin (II) oxide added to the aqueous methanesulfonic acid solution was dissolved as it was, until the $Sn^{2+}$ ion concentration expected from the addition amount was around 300 [g/L], but if the addition amount exceeded it, not only the tin (II) oxide was not dissolved, but also the dissolved amount was decreased. When the tin (II) oxide was added until the $Sn^{2+}$ ion concentration expected from the addition amount was about 400 [g/L], the $Sn^{2+}$ ion concentration in the aqueous tin methanesulfonate solution was decreased to about 50 [g/L].

Further, as can be seen from the graphs in FIGS. 1 to 7, for 2.0-fold MSA, the whole amount of the tin (II) oxide added to the aqueous methanesulfonic acid solution was dissolved as it was, until the $Sn^{2+}$ ion concentration expected from the addition amount was about 200 [g/L], but if the addition amount exceeded it, not only the tin (II) oxide was not dissolved, but also the dissolved amount was decreased. When the tin (II) oxide was added until the $Sn^{2+}$ ion concentration expected from the addition amount was about 300 [g/L], the $Sn^{2+}$ ion concentration in the aqueous tin methanesulfonate solution was decreased to about 50 [g/L].

As can be seen from the graphs in FIGS. 1 to 7, for 2.5-fold MSA, the whole amount of the tin (II) oxide added to the aqueous methanesulfonic acid solution was also dissolved as it was, until the $Sn^{2+}$ ion concentration expected from the addition amount was about 200 [g/L], but if the addition amount exceeded it, not only the tin (II) oxide was not dissolved, but also the dissolved amount was decreased. When the tin (II) oxide was added until the $Sn^{2+}$ ion concentration expected from the addition amount was about 230 [g/L], the $Sn^{2+}$ ion concentration in the aqueous tin methanesulfonate solution was decreased to about 100 [g/L].

As can be seen from the graphs in FIGS. 1 to 7, for 3.0-fold MSA, the whole amount of the tin (II) oxide added to the aqueous methanesulfonic acid solution was also dissolved as it was, until the $Sn^{2+}$ ion concentration expected from the addition amount was about 100 [g/L], but if the addition amount exceeded it, not only the tin (II) oxide was not dissolved, but also the dissolved amount was decreased. When the tin (II) oxide was added until the $Sn^{2+}$ ion concentration expected from the addition amount was about 190 [g/L], the $Sn^{2+}$ ion concentration in the aqueous tin methanesulfonate solution was decreased to about 40 [g/L].

The tin (II) oxide is dissolved in the aqueous tin methanesulfonate solution as a solvent. Therefore, it was predicted that in order to increase the amount of tin (II) oxide dissolved in a certain amount of aqueous solution, any sufficient dissolution of the tin (II) oxide should be expected by preparing an excessive amount of tin methanesulfonate with respect to the number of moles required as a stoichiometric ratio. However, on the contrary to this expectation, it was revealed that the presence of a sufficient excess of methanesulfonic acid rather prevented tin (II) oxide from being dissolved, which could rather achieve only a lower $Sn^{2+}$ ion concentration than the $Sn^{2+}$ ion concentration obtained by adding a less amount of tin (II) oxide; and that in order to achieve a higher $Sn^{2+}$ ion concentration, it was desirable to satisfy the equivalent amount in the stoichiometric ratio, and further maintain the tin methanesulfonate concentration at a lower level such that the concentration was as close to that equivalent amount as possible; and that, for example, when a lower tin methanesulfonate concentration of 1.03-fold MSA was used, a higher $Sn^{2+}$ ion concentration of 450 [g/L] could be easily achieved.

INDUSTRIAL APPLICABILITY

According to the present invention, it is possible to provide a tin (II) oxide solution that can be suitably used for supplementation with tin ions and has a higher tin ion concentration. The present invention is an industrially useful invention.

The invention claimed is:
1. A method comprising a step of dissolving tin (II) oxide in an aqueous methanesulfonic acid solution to produce an aqueous tin methanesulfonate solution,
   wherein a value of B/2A is in a range of from 1.00 to 1.09, in which A is the number of moles of tin (II) oxide; and B is the number of moles of methanesulfonic acid,
   wherein the temperature of the aqueous methanesulfonic acid solution is maintained in the range of from about 30 to 50° C.,
   wherein when tin (II) oxide is completely dissolved in the aqueous methanesulfonic acid solution, a content of tin present as $Sn^{2+}$ ions is in a range of from 300 to 450 g/L, and
   wherein the tin (II) oxide is a tin (II) oxide powder that is added to the aqueous methanesulfonic acid solution, stirred and dissolved to produce the aqueous tin methanesulfonate solution.

2. The method according to claim 1, wherein the value of B/2A is in a range of from 1.01 to 1.05.

3. The method according to claim 1, wherein the tin (II) oxide powder is added to the aqueous methanesulfonic acid solution continuously over 1 to 10 minutes, stirred and dissolved to produce an aqueous tin methanesulfonate solution.

4. The method according to claim 1, wherein the number of moles of tin (II) oxide A is the number of moles of the total amount of tin (II) oxide used for dissolution, and wherein the number of moles of methanesulfonic acid B is the number of moles of the total amount of methanesulfonic acid used for dissolution.

5. A method for supplementing a tin plating solution with tin ions, the method comprising a step of adding the aqueous tin methanesulfonate solution produced by the method for dissolving tin (II) oxide in an aqueous methanesulfonic acid solution to produce an aqueous tin methanesulfonate solution,
wherein a value of B/2A is in a range of from 1.00 to 1.09, in which A is the number of moles of tin (II) oxide; and B is the number of moles of methanesulfonic acid,
wherein the temperature of the aqueous methanesulfonic acid solution is maintained in the range of from about 30 to 50° C.,
wherein when tin (II) oxide is completely dissolved in the aqueous methanesulfonic acid solution, a content of tin present as Sn2+ ions is in a range of from 300 to 450 g/L, and
wherein the tin (II) oxide is a tin (II) oxide powder that is added to the aqueous methanesulfonic acid solution, stirred and dissolved to produce the aqueous tin methanesulfonate solution.

6. A method for supplementing a tin plating solution with tin ions, the method comprising a step of adding the aqueous tin methanesulfonate solution produced by the method according to claim 1 to the tin plating solution.

7. A method for supplementing a tin plating solution with tin ions, the method comprising a step of adding the aqueous tin methanesulfonate solution produced by the method according to claim 2 to the tin plating solution.

8. A method for supplementing a tin plating solution with tin ions, the method comprising a step of adding the aqueous tin methanesulfonate solution produced by the method according to claim 3 to the tin plating solution.

9. A method for supplementing a tin plating solution with tin ions, the method comprising a step of adding the aqueous tin methanesulfonate solution produced by the method according to claim 4 to the tin plating solution.

* * * * *